(12) United States Patent
Mulrooney

(10) Patent No.: US 11,992,681 B2
(45) Date of Patent: May 28, 2024

(54) DEVICES, SYSTEMS, AND METHODS FOR TREATING DISEASE USING ELECTRICAL STIMULATION

(71) Applicant: Phagenesis Limited, Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 66 days.

(21) Appl. No.: 17/455,593

(22) Filed: Nov. 18, 2021

(65) Prior Publication Data
US 2022/0161029 A1 May 26, 2022

Related U.S. Application Data

(60) Provisional application No. 63/198,896, filed on Nov. 20, 2020.

(51) Int. Cl.
*A61N 1/05* (2006.01)
*A61N 1/36* (2006.01)

(52) U.S. Cl.
CPC ............ *A61N 1/3606* (2013.01); *A61N 1/05* (2013.01); *A61N 1/36128* (2013.01)

(58) Field of Classification Search
CPC .... A61N 1/3606; A61N 1/05; A61N 1/36128; A61N 1/0551; A61N 1/0546; A61N 1/0548; A61N 1/0519; A61N 1/06; A61N 1/327; A61N 1/326; A61N 1/362; A61N 1/205; A61N 1/32; A61N 1/325; Y10S 128/922; C08L 2201/12; A61B 18/1492; A61B 2018/0022; A61B 2018/00577
See application file for complete search history.

(56) References Cited

U.S. PATENT DOCUMENTS

| | | | |
|---|---|---|---|
| 803,464 | A | 10/1905 | Beck |
| 1,032,436 | A | 7/1912 | Smith |
| 2,627,096 | A | 2/1953 | Alessi |
| 2,779,985 | A | 2/1957 | Turner et al. |

(Continued)

FOREIGN PATENT DOCUMENTS

| | | |
|---|---|---|
| CA | 2594296 A1 | 3/2006 |
| CN | 203389196 U | 1/2014 |

(Continued)

OTHER PUBLICATIONS

Bath et al., Pharyngeal electrical stimulation for neurogenic dysphagia following stroke, traumatic brain injury or other causes: Main results from the PHADER cohort study, EClinical Medicine 28 (2020) 100608, 9 pages.

(Continued)

*Primary Examiner* — Carl H Layno
*Assistant Examiner* — Anh-Khoa N Dinh
(74) *Attorney, Agent, or Firm* — Fortem IP LLP

(57) ABSTRACT

Electrical stimulation devices and associated systems and methods are disclosed herein. In some embodiments, the electrical stimulation device comprises an elongated member configured to be orally or nasally inserted into a patient's pharynx. The device may further include a conductive element carried by a distal portion of the elongated member and configured to deliver stimulation energy to nearby tissue. The device can include a cover configured to move relative to the conductive elements to selectively cover or expose the conductive elements.

35 Claims, 5 Drawing Sheets

(56) References Cited

U.S. PATENT DOCUMENTS

| | | |
|---|---|---|
| 3,179,995 A | 4/1965 | Hawk |
| 3,630,195 A | 12/1971 | Santomieri |
| 3,839,841 A | 10/1974 | Amplatz |
| 3,894,706 A | 7/1975 | Mizusawa |
| 3,951,136 A | 4/1976 | Wall |
| 4,025,015 A | 5/1977 | Kolic |
| 4,295,618 A | 10/1981 | Morota et al. |
| 4,453,545 A | 6/1984 | Inoue |
| 4,691,883 A | 9/1987 | Kurihara |
| 4,707,906 A | 11/1987 | Posey |
| 4,776,349 A | 10/1988 | Nashef et al. |
| 4,840,337 A | 6/1989 | Zaugg |
| 5,109,870 A | 5/1992 | Silny et al. |
| 5,147,315 A | 9/1992 | Weber |
| 5,179,952 A | 1/1993 | Buinevicius et al. |
| 5,201,903 A | 4/1993 | Corbett et al. |
| 5,372,131 A | 12/1994 | Heinen |
| 5,382,239 A | 1/1995 | Orr et al. |
| 5,389,074 A | 2/1995 | Parker et al. |
| 5,457,852 A | 10/1995 | Liu |
| 5,551,953 A | 9/1996 | Lattin et al. |
| 5,588,424 A | 12/1996 | Insler et al. |
| 5,755,225 A | 5/1998 | Hutson |
| 5,759,490 A | 6/1998 | Malchesky |
| 5,762,638 A | 6/1998 | Shikani et al. |
| 5,800,402 A | 9/1998 | Bierman |
| 5,836,895 A | 11/1998 | Ramsey |
| 5,957,968 A | 9/1999 | Belden et al. |
| 6,006,138 A | 12/1999 | Don |
| 6,148,222 A | 11/2000 | Ramsey |
| 6,259,938 B1 | 7/2001 | Zarychta et al. |
| 6,266,548 B1 | 7/2001 | Lamade et al. |
| 6,366,813 B1 | 4/2002 | Dilorenzo |
| 6,464,697 B1 | 10/2002 | Edwards et al. |
| 6,484,053 B2 | 11/2002 | Leelamanit et al. |
| 6,611,699 B2 | 8/2003 | Krueger |
| 6,613,025 B1 | 9/2003 | Palasis |
| 6,658,294 B1 | 12/2003 | Zadeh et al. |
| 6,804,866 B2 | 10/2004 | Lemke et al. |
| 6,856,822 B2 | 2/2005 | Larsson |
| 7,324,851 B1 | 1/2008 | Dilorenzo |
| 7,598,839 B1 | 10/2009 | Wedley |
| 7,871,430 B2 | 1/2011 | Pavcnik et al. |
| 7,918,828 B2 | 4/2011 | Lundgaard et al. |
| 8,048,062 B2 | 11/2011 | Adams et al. |
| 8,092,433 B2 | 1/2012 | Hamdy |
| 8,876,798 B2 | 11/2014 | Clark et al. |
| 8,968,331 B1 * | 3/2015 | Sochor ............... A61B 17/3468 606/129 |
| 9,895,486 B1 | 2/2018 | Carey-Hench |
| 9,982,742 B2 | 5/2018 | Loewe et al. |
| 10,028,885 B2 | 7/2018 | Martin et al. |
| 10,285,341 B2 | 5/2019 | McCaslin et al. |
| 10,743,810 B2 | 8/2020 | Mulrooney |
| 10,888,690 B2 | 1/2021 | Mulrooney |
| 11,617,881 B2 | 4/2023 | Mulrooney et al. |
| 2001/0054425 A1 | 12/2001 | Bertram |
| 2002/0032468 A1 | 3/2002 | Hill et al. |
| 2002/0065544 A1 | 5/2002 | Smits |
| 2002/0177765 A1 | 11/2002 | Bowe et al. |
| 2003/0036794 A1 | 2/2003 | Ragheb et al. |
| 2004/0034396 A1 | 2/2004 | Asmar et al. |
| 2004/0220645 A1 | 11/2004 | Kretschmer et al. |
| 2004/0230162 A1 | 11/2004 | Tan |
| 2005/0098688 A1 | 5/2005 | Miarka et al. |
| 2005/0137459 A1 | 6/2005 | Chin et al. |
| 2005/0146676 A1 | 7/2005 | Silvestro |
| 2005/0192559 A1 | 9/2005 | Michels et al. |
| 2005/0229933 A1 | 10/2005 | McGrail et al. |
| 2006/0085049 A1 | 4/2006 | Cory et al. |
| 2007/0074728 A1 | 4/2007 | Rea |
| 2007/0089898 A1 | 4/2007 | Potter |
| 2007/0156041 A1 | 7/2007 | Rea |
| 2008/0147013 A1 | 6/2008 | Breton et al. |
| 2008/0249507 A1 | 10/2008 | Hadani |
| 2008/0255441 A1 | 10/2008 | Hadani |
| 2008/0300530 A1 | 12/2008 | Massengale |
| 2009/0062772 A1 | 3/2009 | Wakeford et al. |
| 2009/0223698 A1 | 9/2009 | Gilliland et al. |
| 2009/0276025 A1 | 11/2009 | Burnes et al. |
| 2010/0115739 A1 | 5/2010 | Mathur |
| 2010/0170066 A1 | 7/2010 | Honeycutt |
| 2010/0174170 A1 | 7/2010 | Razavi |
| 2010/0206453 A1 | 8/2010 | Leeflang et al. |
| 2010/0218975 A1 | 9/2010 | Mehan |
| 2010/0317956 A1 | 12/2010 | Kartush |
| 2011/0137374 A1 | 6/2011 | Kieval et al. |
| 2011/0210215 A1 | 9/2011 | Nitsche et al. |
| 2011/0251519 A1 | 10/2011 | Romoscanu |
| 2012/0065469 A1 | 3/2012 | Allyn et al. |
| 2012/0203058 A1 | 8/2012 | Kanapkey et al. |
| 2012/0259208 A1 * | 10/2012 | Bloom ............... A61M 25/0032 128/207.14 |
| 2012/0260921 A1 | 10/2012 | Sangwan |
| 2013/0006323 A1 | 1/2013 | Tal et al. |
| 2013/0197321 A1 | 8/2013 | Wilson |
| 2013/0282078 A1 | 10/2013 | Wacnik |
| 2014/0012235 A1 | 1/2014 | Pinchuk et al. |
| 2014/0128936 A1 | 5/2014 | Laufer et al. |
| 2014/0276663 A1 | 9/2014 | Pinchuk et al. |
| 2014/0288384 A1 * | 9/2014 | Mulrooney ............ A61B 5/037 607/116 |
| 2014/0303617 A1 | 10/2014 | Shimada |
| 2014/0378941 A1 | 12/2014 | Su et al. |
| 2015/0224280 A1 | 8/2015 | Pinchuk et al. |
| 2017/0050014 A1 * | 2/2017 | Rizik ................ A61N 1/0534 |
| 2017/0224986 A1 | 8/2017 | Imran et al. |
| 2017/0312497 A1 | 11/2017 | Mulrooney et al. |
| 2018/0214672 A1 | 8/2018 | Mulrooney |
| 2018/0235533 A1 | 8/2018 | Mulrooney |
| 2019/0038894 A1 | 2/2019 | Bassi et al. |
| 2019/0134380 A1 | 5/2019 | Mulrooney |
| 2019/0134389 A1 | 5/2019 | Mulrooney |
| 2020/0061369 A1 | 2/2020 | Mulrooney et al. |
| 2020/0061370 A1 | 2/2020 | Mulrooney et al. |
| 2020/0179045 A1 | 6/2020 | Levin et al. |
| 2020/0330025 A1 | 10/2020 | Mulrooney |
| 2021/0077784 A1 | 3/2021 | Mulrooney |
| 2021/0077808 A1 | 3/2021 | Mulrooney et al. |
| 2022/0160537 A1 | 5/2022 | Mulrooney |
| 2022/0161030 A1 | 5/2022 | Mulrooney |
| 2022/0313981 A1 | 10/2022 | Mulrooney |
| 2023/0181023 A1 | 6/2023 | Mulrooney |
| 2023/0302244 A1 | 9/2023 | Mulrooney |

FOREIGN PATENT DOCUMENTS

| | | |
|---|---|---|
| CN | 203954394 U | 11/2014 |
| CN | 204319485 U | 5/2015 |
| EP | 0510857 A1 | 10/1992 |
| EP | 0571514 A1 | 12/1993 |
| EP | 1179307 A2 | 2/2002 |
| EP | 2253350 A1 | 11/2010 |
| EP | 2693968 A1 | 2/2014 |
| EP | 3331597 A1 | 6/2018 |
| GB | 2169206 A | 7/1986 |
| GB | 2254253 A | 10/1992 |
| GB | 2294642 A | 5/1996 |
| GB | 2313316 A | 11/1997 |
| GB | 2532044 A | 5/2016 |
| GB | 2541039 A | 2/2017 |
| JP | 5115563 A | 5/1993 |
| JP | 2556694 B2 | 11/1996 |
| JP | 2005312969 A | 11/2005 |
| JP | 2012512722 A | 6/2012 |
| JP | 2014068716 A | 4/2014 |
| WO | 9400050 A1 | 1/1994 |
| WO | 9405361 A1 | 3/1994 |
| WO | 9526777 A1 | 10/1995 |
| WO | 9715349 A1 | 5/1997 |
| WO | 9719667 A1 | 6/1997 |
| WO | 03026741 A1 | 4/2003 |
| WO | 2005051472 A2 | 6/2005 |
| WO | 2006024825 A1 | 3/2006 |

(56) References Cited

FOREIGN PATENT DOCUMENTS

| | | |
|---|---|---|
| WO | 2007129002 A1 | 11/2007 |
| WO | 2009154718 A1 | 12/2009 |
| WO | 2010023579 A1 | 3/2010 |
| WO | 2010071812 A1 | 6/2010 |
| WO | 2010091440 A2 | 8/2010 |
| WO | 2012131303 A1 | 10/2012 |
| WO | 2013109835 A1 | 7/2013 |
| WO | 2014152808 A1 | 9/2014 |
| WO | 2015027094 A1 | 2/2015 |

OTHER PUBLICATIONS

Bath et al., Pharyngeal Electrical Stimulation for Treatment of Dysphagia in Subacute Stroke a Randomized Controlled Trial, Stroke, Jun. 2016, vol. 47, Issue 6, pp. 1562-1570.

Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.

Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.

Essa et al., The BDNF polymorphism VAL66Met may be predictive of swallowing improvement post pharyngeal electrical stimulation in dysphagic stroke patients, Neurogastroenterol Motil, 2017; 27, 7 pages.

European Patent Office, International Search Report and Written Opinion for International Application No. PCT/GB2005/003289, dated Dec. 30, 2005, 14 pages.

European Patent Office, International Search Report and Written Opinion for International Application No. PCT/GB2015/053366, dated Jan. 29, 2016, 13 pages.

European Patent Office, International Search Report and Written Opinion for International Application No. PCT/GB2016/052389, dated Nov. 2, 2016, 15 pages.

European Patent Office, International Search Report and Written Opinion for International Application No. PCT/GB2016/053628, dated Mar. 15, 2017, 12 pages.

European Patent Office, International Search Report and Written Opinion for International Application No. PCT/GB2017/051482, dated Jul. 24, 2017, 8 pages.

European Patent Office, International Search Report and Written Opinion for International Application No. PCT/GB2021/053010, dated Feb. 23, 2022, 13 pages.

European Patent Office, International Search Report and Written Opinion for International Application No. PCT/GB2021/053011, dated Feb. 24, 2022, 16 pages.

Fraser et al., Differential changes in human pharyngoesophageal motor excitability induced by swallowing, pharyngeal stimulation, and anesthesia, Am J Physiol Gastrointest Liver Physiol, 285: G-137-G144, 2003.

Hamdy et al., The cortical topography of human swallowing musculature in health and disease, Nature Medicine, vol. 2, No. 11, Nov. 1996, pp. 1217-1224.

Hamdy et al., Long-term reorganization of human motor cortex driven by short-term sensory stimulation, Nature Neuroscience, vol. 1, No. 1, May 1998, pp. 64-68.

European Patent Office, International Search Report and Written Opinion for International Application No. PCT/GB2020/050934, dated Jul. 20, 2020, 11 pages.

Jayasekeran et al., Adjunctive Functional Pharyngeal Electrical Stimulation Reverses Swallowing Disability After Brain Lesions, Gastroenterology, 2010; vol. 138, No. 5, pp. 1737-1746.

Koestenberger et al., A Pilot Study of Pharyngeal Electrical Stimulation of Orally Intubated ICU Patients with Dysphagia, Neurocrit Care (2020) 32: 532-538.

Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].

Magara et al., Exploring the effects of synchronous pharyngeal electrical stimulation with swallowing carbonated water on cortical excitability in the human pharyngeal motor system, Neurogastroenterol Motil (2016), 11 pages.

European Patent Office, International Search Report and Written Opinion for International Application No. PCT/GB2016/052381, dated Sep. 26, 2016, 10 pages.

Restivo et al., Pharyngeal electrical stimulation device for the treatment of neurogenic dysphagia: technology update, Medical Devices: Evidence and Research, 2018: 11, pp. 21-26.

Restivo et al., Pharyngeal Electrical Stimulation for Dysphagia Associated with Multiple Sclerosis: A Pilot Study, Brain Stimulation 6, 2013, pp. 418-423.

Sasegbon et al., Advances in the Use of Neuromodulation for Neurogenic Dysphagia: Mechanisms and Therapeutic Application of Pharyngeal Electrical Stimulation, Transcranial Magnetic Stimulation, and Transcranial Direct Current Stimulation, American Journal of Speech-Language Pathology, Jul. 2020, vol. 29, pp. 1044-1064.

Scutt et al., Pharyngeal Electrical Stimulation for Treatment of Poststroke Dysphagia: Individual Patient Data Meta-Analysis of Randomised Controlled Trials, Stroke Research and Treatment, 2015, 8 pages.

Suntrup et al., Electrical pharyngeal stimulation for dysphagia treatment in tracheotomized stroke patients: a randomized controlled trial, Intensive Care Med (2015) 41: 1629-1637.

Suntrup-Krueger et al., Electrical pharyngeal stimulation increases substance P level in saliva, Neurogastroenterol Motil (2016) 28, pp. 855-860.

Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.

Fraser et al., "Driving Plasticity in Human Adult Motor Cortex is Associated with Improved Motor Function After Brain Injury", Neuron, vol. 34, May 30, 2002, pp. 831-840.

Gow et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.

Hamdy et al., "Modulation of human swallowing behaviour by thermal and chemical stimulation in health and after brain injury", Neurogastroenterol Motil, vol. 15, No. 1, Feb. 2003, pp. 69-77.

Hamdy et al., "Recovery of Swallowing After Dysphagic Stroke Relates to Functional Reorganization in the Intact Motor Cortex", Gastroenterology, vol. 115, No. 5, Nov. 1998, pp. 1104-1112.

Jasper, Herbert H., "The Ten Twenty Electrode System of the International Federation", Clinical Neurophysiol, vol. 10, pp. 370-375.

Kajii et al., "Sour taste stimulation facilitates reflex swallowing from the pharynx and larynx in the rat", Physiology & Behavior, vol. 77, No. 2-3, 2002, pp. 321-325.

Takeuchi et al., "Electrophysiological and Behavioral Studies of Taste Discrimination in the Axolotl (*Ambystoma mexicanum*)", Physiology & Behavior, vol. 56, No. 1, Jul. 1994, pp. 121-127.

Tutuian et al., "Effects of position on oesophageal function: studies using combined manometry and multichannel Intraluminal impedance", Neurogastroenterol Motil., vol. 15, No. 1, Feb. 2003, pp. 63-67.

Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108,, 1998, pp. 1-16.

Wilmskoetter, Janina, et al., "Cortical and Subcortical Control of Swallowing—Can We Use Information From Lesion Locations to

(56) References Cited

OTHER PUBLICATIONS

Improve Diagnosis and Treatment for Patients With Stroke?", American journal of speech-language pathology vol. 29,2S (2020): 1030-1043. (Year: 2020).

* cited by examiner

DEVICES, SYSTEMS, AND METHODS FOR TREATING DISEASE USING ELECTRICAL STIMULATION

CROSS-REFERENCE TO RELATED APPLICATION(S)

The present application claims the benefit of priority to U.S. Provisional Patent Application No. 63/198,896, titled DEVICES, SYSTEMS, AND METHODS FOR TREATING DISEASE USING ELECTRICAL STIMULATION, filed Nov. 20, 2020, which is incorporated by reference herein in its entirety.

TECHNICAL FIELD

The present disclosure is directed generally to devices, systems, and methods for treating disease using electrical stimulation. Particular embodiments include treating dysphagia by applying electrical stimulation to a target neural population of the patient.

BACKGROUND

Dysphagia is the condition whereby a patient has difficulty in swallowing or is unable to swallow safely. Dysphagia may be caused, for example, by stroke, neurodegenerative diseases, brain tumors or in some cases by other co-morbidities, such as respiratory disorders. It has been reported that between 7 and 10% of all adults older than 50 years of age present with clinically significant dysphagia. Of those over the age of 60, this increases to 14%. In total, 10 million Americans are evaluated each year in clinics and hospitals for swallowing difficulties. It has also been reported that over 51% of institutionalized elderly patients present with oropharyngeal dysphagia.

Swallowing is a rigidly ordered sequence of events that results in the propulsion of food from the mouth through the pharynx and esophagus to the stomach. At the same time, respiration is inhibited and food is prevented from entering into the trachea. Swallowing can be initiated voluntarily, but thereafter it is almost entirely under reflex control. The swallow reflex is typically initiated by sensory impulses from tactile receptors (particularly those located near the opening of the pharynx) being transmitted to certain areas in the medulla. The central integrating areas for swallowing lie in the medulla and lower pons; they are collectively called the swallowing center. Motor impulses travel from the swallowing center to the musculature of the pharynx and upper esophagus via various cranial nerves. This lower swallowing center in the brainstem is under regulatory control by higher center in the cerebral cortex. These higher swallowing centers or regions control the voluntary initiation and modulation of the swallow.

Swallowing occurs in three stages. In the oral or voluntary phase, food is moved towards the back of the mouth by the tongue, and forced into the pharynx, where it stimulates the tactile receptors that initiate the swallowing reflex. In the pharyngeal stage of swallowing, food passes through the pharynx by constriction of the walls of the pharynx, backward bending of the epiglottis, and an upward and forward movement of the larynx and trachea. During the pharyngeal stage, respiration is reflexively inhibited. In the esophageal stage of swallowing, food moves down the esophagus and into the stomach, assisted by one or more peristaltic waves.

Although the main function of swallowing is the propulsion of food from the mouth into the stomach, swallowing also serves as a protective reflex for the upper respiratory tract, preventing unwanted particles from entering the tract. Food or liquid that enters into the airways may act as a locus for infection and this type of infection can be life threatening. For instance, dysphagia after a stroke can be a devastating problem, as it carries a six-fold increased risk of aspiration pneumonia.

Complications that have been associated with dysphagia include pneumonia, malnutrition, dehydration, poorer long-term outcome, increased length of hospital stay, increased rehabilitation time and the need for long-term care assistance, increased mortality, and increased health care costs. These complications impact the physical and social wellbeing of patients, quality of life of both patients and caregivers, and the utilization of health care resources.

In view of the above, there remains a need for improved devices and methods that can treat dysphagia.

SUMMARY

The present technology relates to electrical stimulation devices and associated systems and methods. In particular embodiments, the present technology comprises electrical stimulation devices configured to perform pharyngeal electrical stimulation (PES) to treat one or more conditions. Several embodiments of the present disclosure, for example, are configured to perform PES to treat a patient suffering from neurogenic dysphagia. Electrical stimulation of nerves proximate the patient's pharynx increases activity in the motor cortex and other areas of the brain to facilitate a functional reorganization of the centers in the brain responsible for controlling and coordinating swallow function. The subject technology is illustrated, for example, according to various aspects described below, including with reference to FIGS. 1-3B. Various examples of aspects of the subject technology are described as numbered clauses (1, 2, 3, etc.) for convenience. These are provided as examples and do not limit the subject technology.

1. A device for delivering an electrical stimulus to nerves proximate a body lumen of a human patient, the device comprising:
    an elongated member having a proximal portion configured to be coupled to an energy source and a distal portion configured to be positioned at a treatment site within the body lumen;
    a conductive element carried by the distal portion of the elongated member and configured to be electrically coupled to the energy source to deliver an electrical stimulus to nerves proximate the body lumen at the treatment site; and
    a cover, at least a portion of which is disposed at the distal portion of the elongated member, wherein the cover is movable between (a) a first position in which the cover is positioned over the conductive element, and (b) a second position in which the conductive element is exposed.

2. The device of Clause 1, wherein the cover comprises an elongated shaft configured to be slidably positioned over the elongated member.

3. The device of Clause 1 or Clause 2, further comprising a retaining structure fixed to the cover and configured to releasably engage the elongated member to fix a position of the cover relative to the elongated member.

4. The device of any one of Clauses 1 to 3, further comprising an interface coupled to the cover and configured to be positioned at an extracorporeal location when the distal portion of the elongated member is positioned at the treatment site, wherein the interface is configured to be manipulated by an operator to move the cover between the first and second positions.

5. The device of any one of Clauses 1 to 4, further comprising a stop configured to engage the cover to releasably secure the cover in the first position.

6. The device of any one of Clauses 1 to 5, further comprising a stop configured to engage the cover to releasably secure the cover in the second position.

7. The device of any one of Clauses 1 to 6, wherein the elongated member defines a lumen, and wherein the device further comprises:
an elongated shaft configured to be slidably positioned through the lumen of the elongated member; and
a coupler configured to be positioned at an extracorporeal location when the distal portion of the elongated member is positioned at the treatment site, wherein the coupler is configured releasably fix a position of the elongated shaft relative to the elongated member.

8. The device of Clause 7, wherein the elongated shaft has a proximal portion and a distal portion configured to be positioned within the patient's stomach, and wherein the elongated shaft is configured to deliver nutrients to the stomach.

9. The device of any one of Clauses 1 to 8, wherein the treatment site is within a pharynx of the patient.

10. The device of any one of Clauses 1 to 9, wherein the electrical stimulus is configured to treat dysphagia.

11. A medical device comprising:
a stimulation device configured to be inserted into a body lumen of a patient, the stimulation device comprising an elongated member having a proximal portion, a distal portion, and an electrode carried by the distal portion, wherein the distal portion of the elongated member is configured to be positioned at a treatment site within the body lumen;
a cover, at least a portion of which is disposed at the distal portion of the elongated member, wherein the cover is movable between (a) a first position in which the cover is positioned over the electrode, and (b) a second position in which the electrode is exposed.

12. The medical device of Clause 11, wherein the cover is configured to slide over the electrode.

13. The medical device of Clause 11 or Clause 12, wherein the cover is configured to extend around a full circumference of the elongated member.

14. The medical device of Clause 11 or Clause 12, wherein the cover is configured to extend around less than a full circumference of the elongated member.

15. The medical device of any one of Clauses 11 to 14, wherein the first position is distal of the second position.

16. The medical device of any one of Clauses 11 to 15, further comprising a slider coupled to a proximal end portion of the cover, the slider being configured to be manipulated by an operator to adjust a position of the cover relative to the electrode.

17. The medical device of any one of Clauses 11 to 16, wherein the body lumen of the patient is a pharynx.

18. The medical device of any one of Clauses 11 to 17, wherein the stimulation device is configured to electrically stimulate nerves proximate an oropharyngeal region of the pharynx to treat dysphagia.

19. The medical device of any one of Clauses 11 to 18, wherein the electrode is a first electrode, and wherein the stimulation device further comprises a second electrode longitudinally spaced apart from the first electrode along a longitudinal dimension of the elongated member.

20. A method for stimulating nerves proximate a pharynx of a human patient, the method comprising:
positioning a distal portion of a stimulation device at a treatment site within the pharynx, the distal portion including an electrode configured to be electrically coupled to an energy source;
moving a cover from a first position in which the cover is positioned over the electrode to a second position in which the electrode is exposed; and
stimulating nerves proximate the treatment site by delivering an electric stimulus via the electrode.

21. The method of Clause 20, further comprising moving the cover from the second position to the first position after stimulating the nerves.

22. The method of Clause 20 or Clause 21, further comprising delivering nutrients to the patient's stomach via a feeding tube of the stimulation device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

As previously mentioned, the present technology relates to electrical stimulation devices and associated systems and methods. In particular embodiments, the present technology comprises electrical stimulation devices configured to perform PES to treat one or more conditions. Several embodiments of the present disclosure, for example, are configured to perform PES to treat a patient suffering from neurogenic dysphagia. Patients with dysphagia may also have reflux. Regular reflux may bring highly acidic materials from the stomach to the area in the pharynx where the electrodes of the stimulation device are located. Existing stimulation devices for treating dysphagia are often coupled with feeding tubes and left inserted in the patient for days, while only used for stimulation for several minutes a day. As such, the electrodes remain exposed to the acidic materials for an extended period of time, which can be detrimental to the performance of the device. For example, the highly acidic materials may cause corrosion and pitting of the electrodes, which can decrease the surface quality of the electrodes and therefore reduce the quality of contact with patient tissue. Also, the highly acidic materials may coat the electrodes with biomaterials/food residues that are not conductive, thus affecting the coverage and intensity of the electric field generated by the electrodes or altogether preventing stimulation. To address the foregoing challenges, the stimulation devices of the present technology include a movable cover for shielding the electrodes from the local environment unless stimulation is needed.

I. System Overview

Figure 1:
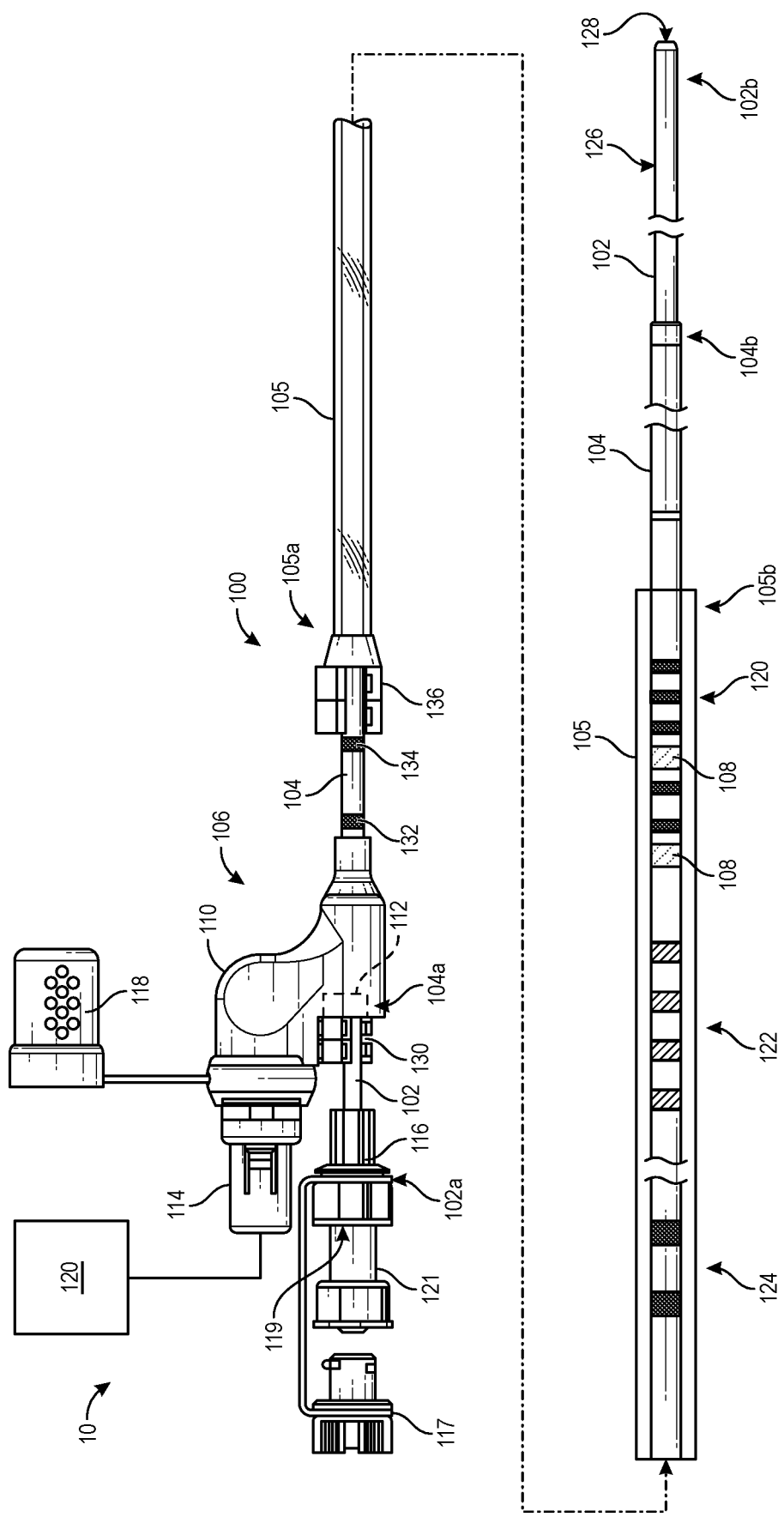
FIG. 1 depicts an electrical stimulation system in accordance with several embodiments of the present technology.

FIG. 1 depicts a treatment system 10 configured in accordance with several embodiments of the present technology. The system 10 may comprise a device 100 configured to provide intraluminal electrical stimulation to a patient suffering from a medical condition, and a current generator 120 configured to be electrically coupled to the device 100. The device 100 can include a handle assembly 106, a first elongated shaft 102 (or "first shaft 102"), and a second elongated shaft 104 (or "second shaft 104") configured to slidably receive the first shaft 102 therethrough. The first shaft 102 can be a flexible tube configured to deliver nutrients to the patient. For example, in some embodiments the first shaft 102 comprises a nasogastric feeding tube. Each of the first and second shafts 102, 104 have a proximal portion 102a and 104a, respectively, coupled to the handle assembly 106, and a distal portion 102b and 104b, respectively, configured to be positioned within an upper gastrointestinal tract of the patient. As depicted in FIGS. 2 and 3, when the device 100 is inserted into the patient, the distal portion 102b of the first shaft 102 is configured to be positioned within the patient's stomach, and the distal portion 104b of the second shaft 104 is configured to be positioned at a treatment site within the patient's pharynx. The device 100 further includes one or more conductive elements 108 carried by the distal portion 104b of the second shaft 104 and configured to deliver stimulation energy to nerves proximate the treatment site. As described in greater detail herein, the device 100 further includes a cover 105 configured to move relative to the conductive elements 108 to prevent unnecessary exposure of the conductive elements 108 to the local environment between treatment sessions.

As shown in FIG. 1, the handle assembly 106 can include a hub 110 and one or more connectors and/or accessory components configured to be removably coupled to the hub 110. The hub 110 can include a housing having a first portion fixedly coupled to the proximal portion 104a of the second shaft 104, and a second portion configured to house one or more electrical components. In some embodiments, the second portion of the housing is positioned laterally of the first portion of the housing. The hub 110 may further include an electrical connector 114 at the second portion that provides an electrical interface between the second shaft 104 and the current generator 120.

In some embodiments, the device 100 includes a connector 116 coupled to the proximal portion 102a of the first shaft 102 and having one or more ports, such as port 119, configured to be coupled to one or more accessory devices or systems. For example, the port 119 may be configured to be releasably coupled to an enteral feeding set (not shown) for delivering nutrients through the first elongated shaft 102 into the patient's stomach. Additionally or alternatively, the port 119 can be configured to be releasably coupled to a guidewire assembly. For example, the port 119 can be configured to receive a guidewire (not visible) therethrough to assist with inserting the device 100 into the patient. The guidewire assembly can include a guidewire grip 121 coupled to the proximal end portion of the guidewire. In some embodiments, the connector 116 includes one or more additional ports, such as a port configured to be fluidly coupled to a syringe or other fluid source and/or pressure source. The connector 116 may further comprise a cap 117 tethered to the connector 116 and configured to be secured over the port 119 when not in use.

As previously mentioned, the first shaft 102 is configured to be inserted through a lumen of the second shaft 104. In use, the distal portion 102b of the first shaft 102 can be inserted into an opening at the proximal portion 104a of the second shaft 104 that is fixed to the hub 110. In some embodiments, the device 100 includes a sealing member (not visible) at the hub 110 that engages the first and second shafts 102, 104 to prevent fluid from within a patient being drawn up within a space between the first and second shafts 102, 104 by way of capillary action when the second shaft 104 is removed from the patient. The sealing member may also be configured to clean any matter off of the first shaft 102 as it is withdrawn from the patient.

The first shaft 102 can have an atraumatic distal tip for patient comfort and ease of inserting the first shaft 102 into the patient. The first shaft 102 can have an opening 128 at its distal end and/or one or more apertures 126 extending through the sidewall along the distal portion 102b of the first shaft 102. Nutrients can be dispersed from the first shaft 102 into the patient's stomach via the one or more apertures 126 and/or the opening 128.

Each of the conductive elements 108 may comprise an electrode, an exposed portion of a conductive material, a printed conductive material, and other suitable forms. In some embodiments, for example as shown in FIG. 1, the conductive elements 108 comprise a pair of ring electrodes configured to deliver bipolar stimulation energy. The conductive elements 108 can be crimped, welded, or otherwise adhered to an outer surface of the second shaft 104. In some embodiments, the conductive elements 108 comprise a flexible conductive material disposed on the second shaft 104 via printing, thin film deposition, or other suitable techniques. While the device 100 shown in FIG. 1 includes two conductive elements 108, in some embodiments the device 100 may include more or fewer than two conductive elements 108. For example, the device 100 may comprise a single conductive element 108 configured to generate a monopolar electric field. Such embodiments include a neutral or dispersive electrode electrically connected to the current generator 120 and positioned on the patient's skin. In some embodiments, the device 100 may include three or more conductive elements 108 spaced apart along a longitudinal axis of the second shaft 104.

The device 100 may include one or more conductive leads (not visible) extending between a proximal portion of the device 100, such as the hub 110, and the conductive elements 108. In some embodiments, for example, the conductive leads comprise two wires, each extending distally from the hub 110 through a channel (the same channel or different channels) in the second shaft 104 to a corresponding one of the conductive elements 108. The channel(s), for example, can extend longitudinally within a sidewall of the shaft 104. The conductive leads can be insulated along all or a portion of their respective lengths.

In some embodiments, the device 100 is configured such that a position of the second shaft 104 can be fixed relative to a position of the first shaft 102 (or vice versa). The position of the first shaft 102 relative to the second shaft 104 may be adjusted prior to insertion of the device 100 into the patient. Once adjustment is complete, the relative positions of the first shaft 102 and second shaft 104 may be substantially fixed. For example, as shown in FIG. 1, the proximal portion 100a of the device 100 can include a retaining structure 130 configured to be coupled to the hub 110 and/or the proximal portions 102a, 104a of one or both of the second shaft 104 and the first shaft 102. The retaining structure 130 can have a first portion on or through which the second shaft 104 and/or first shaft 102 may be movably or fixedly positioned, and a second portion moveable relative to the first portion. When the second portion is in an open position (as shown in FIG. 1), the first shaft 102 and the second shaft 104 can move longitudinally relative to one another. When the second portion is in a closed position (not shown), the longitudinal and/or radial positions of the first shaft 102 and the second shaft 104 are substantially fixed relative to one another.

The retaining structure 130 may be fixed to one of the first shaft 102 or the second shaft 104 and, at least in the open configuration, allow movement of the other of the first shaft 102 and the second shaft 104. In some embodiments, for example as shown in FIG. 1, the proximal portion of the second shaft 104 is fixed to the retaining structure 130 and the proximal portion of the first shaft 102 is slidably received by the first portion when the device 100 is assembled and the second portion is in an open position. When the second portion is in a closed position, the second portion engages the first shaft 102 and fixes the first shaft 102 relative to the second shaft 104, the hub 110, and/or the retaining structure 130.

In any case, the portion of the retaining structure 130 configured to engage the first and/or second shafts 102, 104 can comprise a high friction thermoplastic elastomer liner that engages the proximal portion of the first shaft 102 when the second portion is in the closed position. The liner can be configured to reduce the compressive force required to fix the first shaft 102 and thereby prevent pinching of the first shaft 102. Other suitable shapes, materials, positions, and configurations for the retaining structure 130 are possible. For example, the retaining structure 130 can comprise one or more magnets, a screw and threaded insert, a radial compression clip, and/or others to fix the proximal portion of the first shaft 102 to the retaining structure 130, the hub 110, and/or the second shaft 104.

As previously mentioned, the proximal portion of the device 100 and/or second shaft 104 is configured to be electrically coupled to a current generator 120 for delivering electric current to the conductive elements 108. The current generator 120, for example, can include a power source and a controller. The controller includes a processor coupled to a memory that stores instructions (e.g., in the form of software, code or program instructions executable by the processor or controller) for causing the power source to deliver electric current according to certain parameters provided by the software, code, etc. The power source of the current generator 120 may include a direct current power supply, an alternating current power supply, and/or a power supply switchable between a direct current and an alternating current. The current generator 120 can include a suitable controller that can be used to control various parameters of the energy output by the power source or generator, such as intensity, amplitude, duration, frequency, duty cycle, and polarity. Instead of or in addition to a controller, the current generator can include drive circuitry. In such embodiments, the current generator can include hardwired circuit elements to provide the desired waveform delivery rather than a software-based generator. The drive circuitry can include, for example, analog circuit elements (e.g., resistors, diodes, switches, etc.) that are configured to cause the power source to deliver electric current according to the desired parameters. For example, the drive circuitry can be configured to cause the power source to deliver periodic waveforms. In some embodiments, the drive circuitry can be configured to cause the power source to deliver a unipolar square wave.

The current generator 120 may be configured to provide a stimulation energy to the conductive elements 108 that has an intensity, amplitude, duration, frequency, duty cycle, and/or polarity such that the conductive elements 108 apply an electric field at the treatment site that promotes neuroplasticity in the areas of the brain associated with swallowing control. Without being bound by theory, it is believed that the treatment energy of the present technology induces and accelerates a cortical reorganization process whereby responsibility for the control and coordination of swallowing activity is moved from the damaged area of the brain to a complementary area of the cortical centers with intact function. The treatment energy of the present technology may also increase local levels of swallow-related neurotransmitters in the pharynx, such as in the oropharynx.

The controller can automatically vary the voltage (to a maximum of 250V) in order to deliver the set current. In some embodiments, the only user adjustable parameter is the stimulation intensity which is derived during treatment level optimization prior to every treatment. Patient specific threshold levels are determined by establishing a sensory threshold followed by measurement of the maximum tolerated stimulation intensity. The controller may automatically calculate the correct stimulation level from the sensory threshold and maximum tolerated stimulation intensity and sets this as the output. The current generator 120 can provide, for example, a current of about 1 mA to about 50 mA, about 1 mA to about 40 mA, about 1 mA to about 30 mA, about 1 mA to about 20 mA, or about 1 mA to about 10 mA, at a frequency of about 1 Hz to about 50 Hz, about 1 Hz to about 40 Hz, about 1 Hz to about 30 Hz, about 1 Hz to about 20 Hz, about 1 Hz to about 10 Hz, about 2 Hz to about 8 Hz, about 1 Hz, about 2 Hz, about 3 Hz, about 4 Hz, about 5 Hz, about 6 Hz, about 7 Hz, about 8 Hz, about 9 Hz, or about 10 Hz, and having a pulse width of about 150 μS to about 250 μS, about 175 μS to about 225 μS, or about 200 μS.

The current generator 120 may also be configured to monitor contact quality between the conductive elements 108 and patient tissue during treatment set up/optimization and throughout the treatment process. In some embodiments, the current generator 120 records and stores patient information and includes a USB port to enable downloading of patient data. The current generator may include a touch screen user interface and software to guide a user through the treatment process.

According to some embodiments, for example as shown in FIG. 1, the device 100 may further include a cover 105, at least a portion of which is disposed at the distal portion of the second shaft 104 at or near the conductive elements 108. For example, in some embodiments the cover 105 comprises an elongated tubular member slidably positioned over the second shaft 104. The tubular member can extend between a proximal portion 105a at or near the handle assembly 106 and a distal portion 105b at or near the conductive elements 108. The tubular member can be movable between a first position in which the conductive elements 108 are covered and a second position in which the conductive elements 108 are exposed. For example, in some embodiments, when the cover 105 is in the first position (as shown in FIG. 1), the tubular member extends over and distally beyond the conductive elements 108, thus separating the conductive elements 108 from a surrounding environment. In the second position, the tubular member may be withdrawn relative to the first position such that a distal end of the tubular member is proximal of the conductive elements 108.

The device 100 can also include an interface 136 coupled to a proximal end of the tubular member and configured to be manipulated by an operator to move the tubular member between the first and second positions and/or to fix a position of the cover 105 relative to the second shaft 104. For example, the interface 136 may comprise a retaining structure fixed to the proximal end of the cover 105. The retaining structure can have an open position in which the cover 105 and retaining structure can slide longitudinally relative to the second shaft 104, and a closed position in which the retaining structure is secured to the second shaft 104 such that the cover 105 is substantially fixed in place relative to the second shaft 104.

Figure 2A:
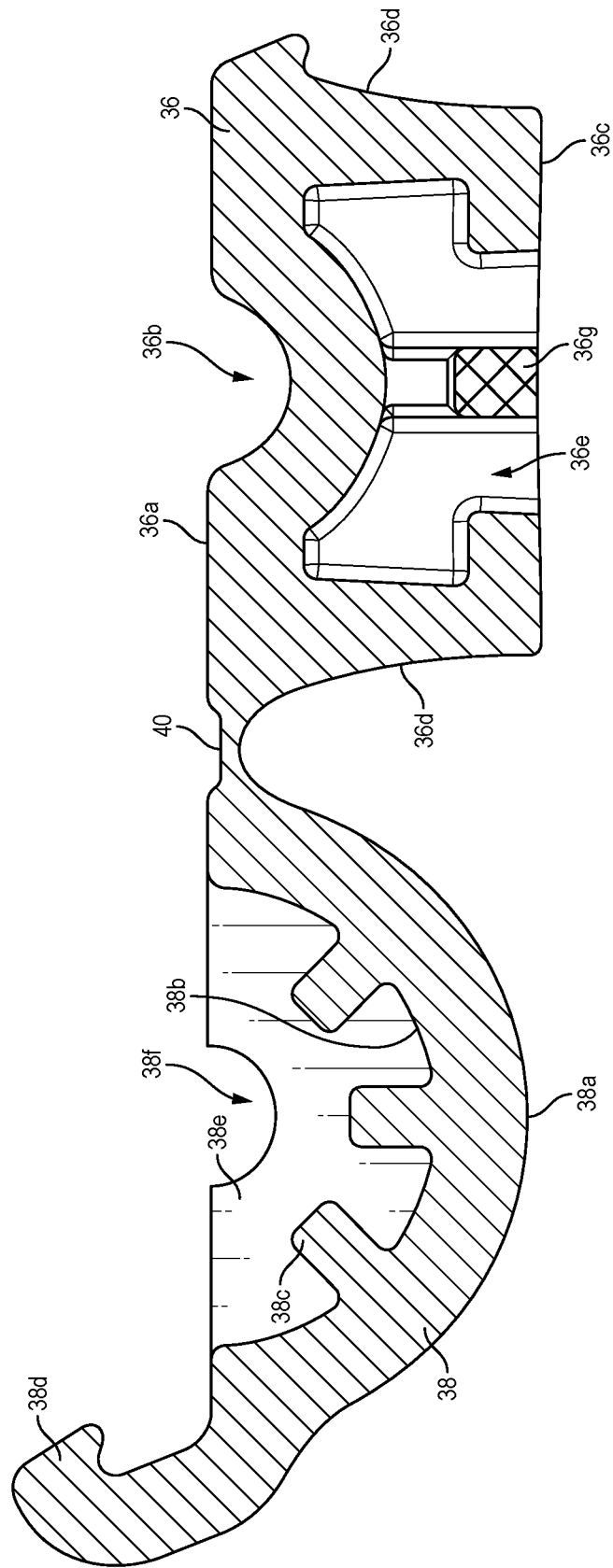
FIGS. 2A and 2B are different views of an interface configured in accordance with several embodiments of the present technology.
Figure 2B:
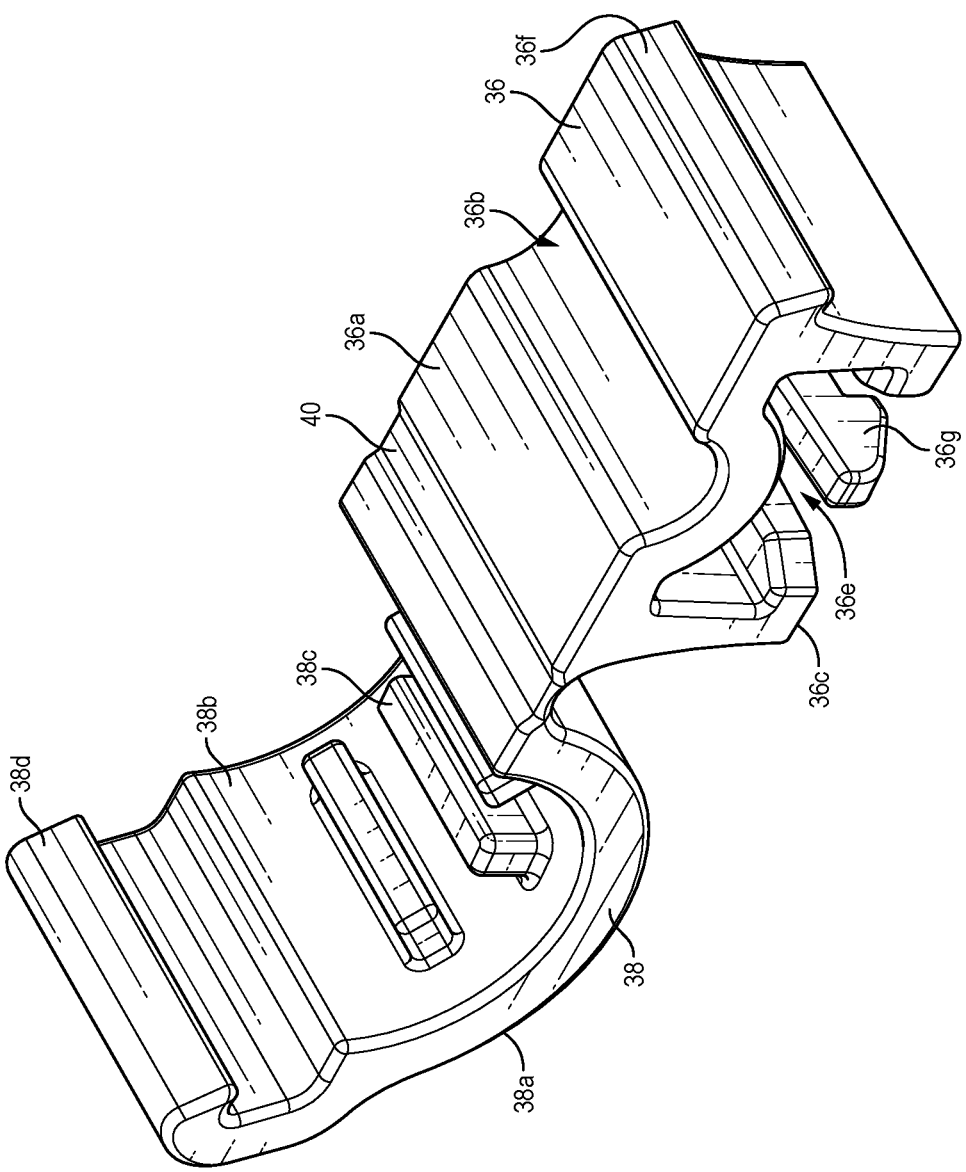

In some embodiments, the interface 136 comprises a retaining clip 34 as illustrated in FIGS. 2A and 2B. The retaining clip 34 can comprise a first portion 36 and a second portion 38 coupled to the first portion at a joint 40 and movable relative to the first portion 36. For example, the joint 40 can be a living hinge. The retaining clip 34 can comprise a polymer, such as polypropylene, and/or other suitable materials.

The first portion 36 of the retaining clip 34, when viewed in cross section, can have a flat top surface 36*a* with a semi-circular cut-out 36*b* therethrough for receiving a part of the second shaft 104. A bottom surface 36*c* can be arranged parallel or substantially parallel to the top surface 36*a*. The bottom surface 36*c* is connected to the top surface by a pair of curved sidewalls 36*d* extending upwardly and outwardly from the edges of the bottom surface 36*c* to the edges of the top surface 36*a*. Each of the sidewalls 36*d* can form a substantially L-shape, as viewed in cross-section, by virtue of a recess 36*e* in the first portion 36 of the retaining clip 34. The recess 36*e* permits the retaining clip 34 to slide on to a mounting formation (not shown) with lateral movement constrained by the L-shape of the sidewalls 36*d*. A resilient finger 36*g* on the first portion 36 of the retaining clip 34 can engage with a recess in the second shaft 104, the hub 110, and/or another portion of the device 100 to restrain longitudinal movement of the retaining clip 34 relative to the second shaft 104, the hub 110, and/or another portion of the device 100. The sidewall 36*d* positioned farthest away from the joint 40 is provided with a ridge 36*f* to, when the retaining clip 34 is closed, hold the first 36 and second 38 portions of the retaining clip 34 in engagement with the second shaft 104.

The second portion 38 of the retaining clip 34 can have a curved top wall 38*a* spaced apart from a curved bottom wall 38*b*. One end of the curved top wall 38*a* can be joined to the joint 40. In some embodiments, the curved bottom wall 38*b* defines a plurality of ribs 38*c* extending outwardly. The end of the curved bottom wall 38*b* opposite the joint 40 can be provided with a spring clip 38*d* which is co-operable, when the retaining clip 34 is closed, with the ridge 36*f* of the first portion 36 of the retaining clip 34.

In some embodiments, the plurality of ribs 38*c* are covered by an elastomer insert 38*e* insertable into the second portion 38 of the retaining clip 34. The insert 38*e* can be deformable and comprises a channel 38*f* which engages against the cover 105 when the retaining clip 34 is closed. The high co-efficient of friction of the elastomer insert 38*e* inhibits longitudinal movement of the cover 105 relative to the retaining clip 34 and second shaft 104. The elastomer insert 38*e* is not shown in FIG. 2B.

The second shaft 104 can include one or more markings or other indicators that indicate locations along the longitudinal axis of the second shaft 104 where, if positioned there, the cover 105 would be in a covered or uncovered position. For example, the second shaft 104 can include a first marking 134 denoting a first position of the cover 105 in which the cover is covering the conductive elements 108 and a second marking 132 proximal of the first marking 134 and denoting a second position of the cover 105 in which the conductive elements 108 are exposed. In those embodiments utilizing a retaining clip, for example, the retaining clip can be moved between the first and second markings 134, 132 and clamped down at one of the markings when fixation of the cover 105 in the corresponding position along the second shaft 104 is desired. Additionally or alternatively, the device 100 can include a first stop (e.g., a ridge, protrusion, recess, etc.) on the second shaft 104 configured to engage the cover 105 and/or interface 136 to releasably secure the cover 105 in the first position, and a second stop (e.g., a ridge, protrusion, recess, etc.) on the second shaft 104 configured to engage the cover 105 and/or interface 136 to releasably secure the cover 105 in the second position.

The cover 105 can have other suitable configurations and arrangements. For example, in some embodiments the cover 105 can be configured to rotate about the circumference of the second shaft 104 between first and second positions to cover and uncover the conductive elements 108.

Example Methods of Use

Without being bound by theory, it is believed that increasing peripheral (sensory) feedback to higher brain centers is a key factor to swallowing rehabilitation. As such, the device 100 of the present technology is configured to stimulate sensory nerves associated with swallowing, thereby inducing and accelerating a cortical reorganization process whereby responsibility for the control and coordination of swallowing activity is moved from the damaged area of the brain to a complementary area of the cortical centers of the brain with intact function. It is also believed that the stimulation energy of the present technology can increase local levels of swallow-related neurotransmitters in the pharynx, such as in the oropharynx.

Figure 3A:
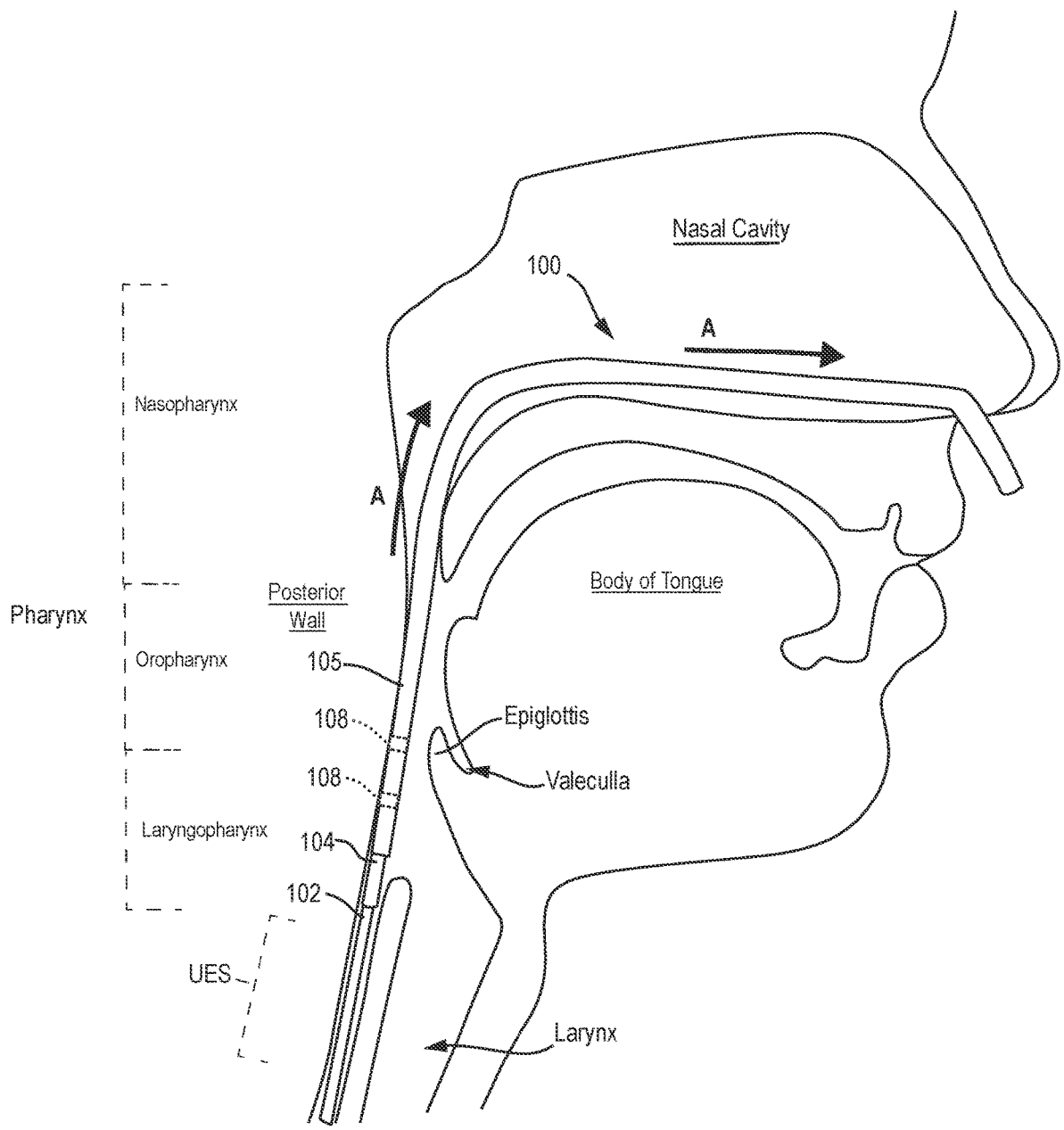
FIGS. 3A and 3B depict an electrical stimulation device trans nasally inserted into a pharynx of a patient in accordance with several embodiments of the present technology.
Figure 3B:
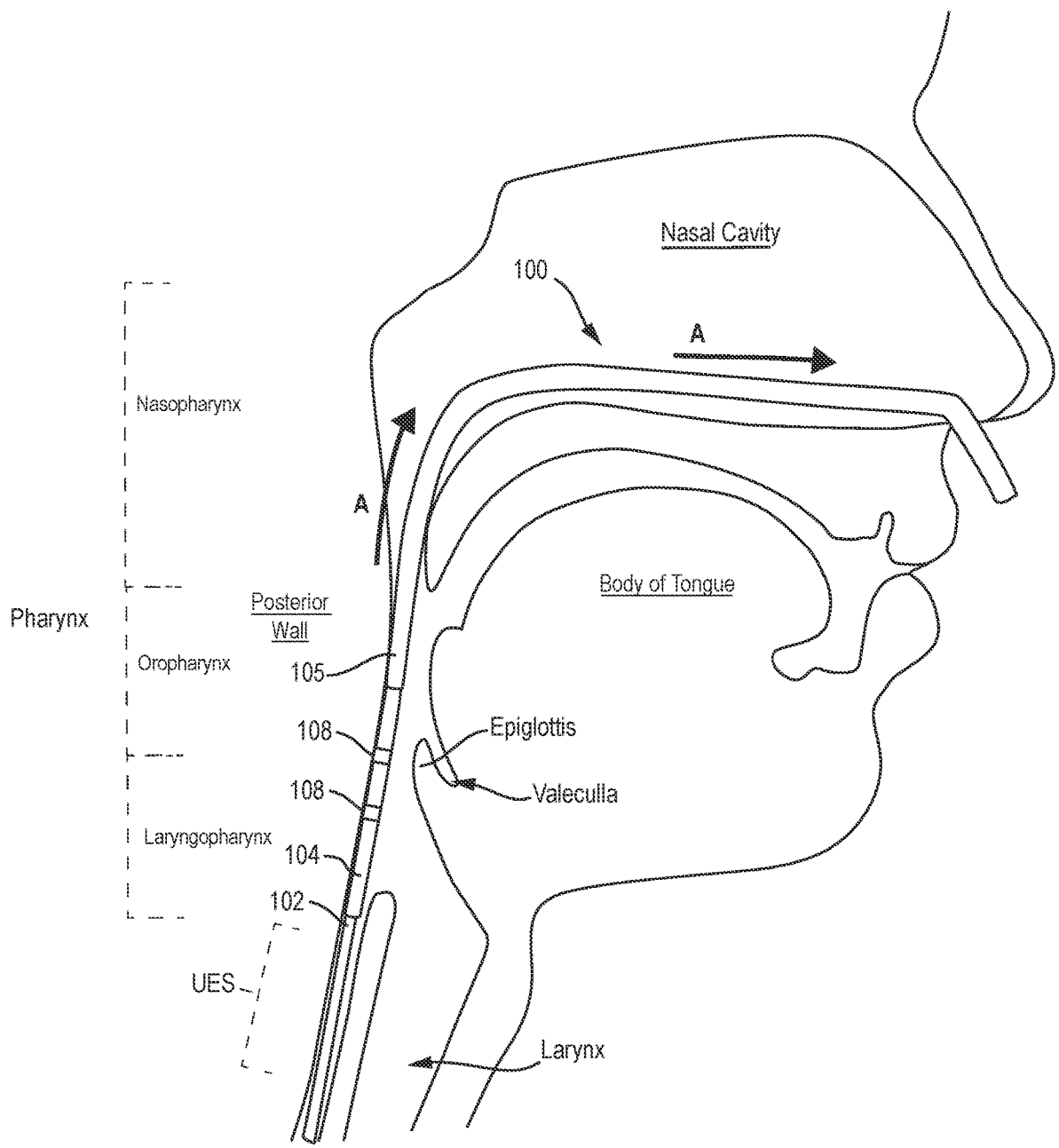

FIG. 3A is a fragmentary sagittal view of a patient's throat with a device 100 of the present technology inserted through the patient's nasal cavity into the pharynx. As shown, during a given treatment, the distal portion of the second shaft 104 is positioned at a treatment site in the pharynx. The device 100 may be inserted with the cover 105 extending over the conductive elements 108, as shown in FIG. 3A, such that the cover 105 is positioned between the conductive elements 108 and the posterior pharyngeal wall. As shown in FIG. 3B, the cover 105 can be withdrawn relative to the second shaft 104 to expose the conductive elements 108 at the treatment site. The conductive elements 108 can be positioned in apposition with the posterior pharyngeal wall along the oropharynx and/or laryngopharynx. In some embodiments, the conductive elements 108 are positioned at a position along the pharynx that is equivalent to the junction between the C3 and C4 cervical vertebrae. Accordingly, when energy is delivered to the conductive elements 108 by the current generator 120, the conductive elements 108 emit an electric field that flows through the posterior wall of the pharynx, the base of the tongue, the epiglottis, and the region above the larynx. Each of these regions includes a high density of targeted sensory nerves for treating dysphagia, including the pharyngeal plexus, the superior laryngeal branch of the vagus nerve, the lingual branch of the glossopharyngeal nerve, the internal branch of the superior laryngeal nerve, and/or the external branch of the superior laryngeal nerve.

After the stimulation energy is delivered, the cover 105 can be advanced distally over the conductive elements 108, thereby protecting the conductive elements 108 from the surrounding environment between treatments.

In some embodiments, the first and/or second shafts 102, 104 can comprise one or more indicators (such as indicators 120, 122, and 124 in FIG. 1) configured to facilitate insertion and positioning of the device 100 within the patient. For example, the indicator can comprise one or more visual markings that, when viewed through the patient's oral cavity, indicate the conductive elements 108 are properly positioned or that the second shaft 104 (and/or conductive elements 108) should be inserted further or withdrawn. In some embodiments, the indicator comprises one or more circumferential markings (such as one or more colored bands) printed on the second shaft 104.

When the conductive elements 108 are in a desired position, stimulation energy is delivered to the treatment site. In some embodiments, the delivered current is a unipolar square wave having an amplitude between 1 mA and 50 mA, a frequency of 5 Hz, and a pulse duration of 200 μS. Each treatment session can have a duration between 5 minutes and 20 minutes. For example, the treatment session can have a duration of 10 minutes. In some embodiments, a patient can undergo a single treatment per day over the course of multiple days of treatment. For example, a patient can undergo one treatment session per day for three to six consecutive days. In some embodiments, the patient may undergo multiple treatment sessions per day and/or per week. Still, other current parameters and treatment parameters are possible.

CONCLUSION

Although many of the embodiments are described above with respect to systems, devices, and methods for electrically stimulating a pharynx of a patient to treat a patient suffering from dysphagia, the technology is applicable to other applications and/or other approaches. For example, the device may be used to treat other conditions, or used to apply a different form of energy (such as ablation energy). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the terms "generally," "substantially," "about," and similar terms are used as terms of approximation and not as terms of degree, and are intended to account for the inherent variations in measured or calculated values that would be recognized by those of ordinary skill in the art.

I claim:

1. A device for delivering an electrical stimulus to nerves proximate a body lumen of a human patient, the device comprising:
    an elongated member having a proximal portion configured to be coupled to an energy source and a distal portion configured to be positioned at a treatment site within the body lumen;
    a conductive element carried by the distal portion of the elongated member and configured to be electrically coupled to the energy source to deliver an electrical stimulus to nerves proximate the body lumen at the treatment site;
    a cover, at least a portion of which is disposed at the distal portion of the elongated member, wherein the cover is movable between (a) a first position in which the cover is positioned over the conductive element, and (b) a second position in which the conductive element is exposed; and
    a stop configured to engage the cover to releasably secure the cover in the first position.

2. The device of claim 1, wherein the cover comprises an elongated shaft configured to be slidably positioned over the elongated member.

3. The device of claim 1, further comprising a retaining structure fixed to the cover and configured to releasably engage the elongated member to fix a position of the cover relative to the elongated member.

4. The device of claim 1, further comprising an interface coupled to the cover and configured to be positioned at an extracorporeal location when the distal portion of the elongated member is positioned at the treatment site, wherein the interface is configured to be manipulated by an operator to move the cover between the first and second positions.

5. The device of claim 1, wherein the stop is configured to engage the cover to releasably secure the cover in the second position.

6. The device of claim 1, wherein the elongated member defines a lumen, and wherein the device further comprises:
    an elongated shaft configured to be slidably positioned through the lumen of the elongated member; and
    a coupler configured to be positioned at an extracorporeal location when the distal portion of the elongated member is positioned at the treatment site, wherein the coupler is configured releasably fix a position of the elongated shaft relative to the elongated member.

7. The device of claim 6, wherein the elongated shaft has a proximal portion and a distal portion configured to be positioned within the patient's stomach, and wherein the elongated shaft is configured to deliver nutrients to the stomach.

8. The device of claim 1, wherein the treatment site is within a pharynx of the patient.

9. The device of claim 1, wherein the electrical stimulus is configured to treat dysphagia.

10. A medical device comprising:
a stimulation device configured to be inserted into a body lumen of a patient, the stimulation device comprising an elongated member having a proximal portion, a distal portion, and an electrode carried by the distal portion, wherein the distal portion of the elongated member is configured to be positioned at a treatment site within the body lumen;
a cover, at least a portion of which is disposed at the distal portion of the elongated member, wherein the cover is movable between (a) a first position in which the cover is positioned over the electrode, and (b) a second position in which the electrode is exposed; and
a slider coupled to a proximal end portion of the cover, the slider being configured to be manipulated by an operator to adjust a position of the cover relative to the electrode.

11. The medical device of claim 10, wherein the cover is configured to slide over the electrode.

12. The medical device of claim 10, wherein the cover is configured to extend around a full circumference of the elongated member.

13. The medical device of claim 10, wherein the cover is configured to extend around less than a full circumference of the elongated member.

14. The medical device of claim 10, wherein the first position is distal of the second position.

15. The medical device of claim 10, wherein the body lumen of the patient is a pharynx.

16. The medical device of claim 15, wherein the stimulation device is configured to electrically stimulate nerves proximate an oropharyngeal region of the pharynx to treat dysphagia.

17. The medical device of claim 10, wherein the electrode is a first electrode, and wherein the stimulation device further comprises a second electrode longitudinally spaced apart from the first electrode along a longitudinal dimension of the elongated member.

18. A device for delivering an electrical stimulus to nerves proximate a body lumen of a human patient, the device comprising:
an elongated member having a proximal portion configured to be coupled to an energy source and a distal portion configured to be positioned at a treatment site within the body lumen;
a conductive element carried by the distal portion of the elongated member and configured to be electrically coupled to the energy source to deliver an electrical stimulus to nerves proximate the body lumen at the treatment site;
a cover, at least a portion of which is disposed at the distal portion of the elongated member, wherein the cover is movable between (a) a first position in which the cover is positioned over the conductive element, and (b) a second position in which the conductive element is exposed; and
a stop configured to engage the cover to releasably secure the cover in the second position.

19. The device of claim 18, wherein the cover comprises an elongated shaft configured to be slidably positioned over the elongated member.

20. The device of claim 18, further comprising a retaining structure fixed to the cover and configured to releasably engage the elongated member to fix a position of the cover relative to the elongated member.

21. The device of claim 18, further comprising an interface coupled to the cover and configured to be positioned at an extracorporeal location when the distal portion of the elongated member is positioned at the treatment site, wherein the interface is configured to be manipulated by an operator to move the cover between the first and second positions.

22. The device of claim 18, wherein the stop is configured to engage the cover to releasably secure the cover in the first position.

23. The device of claim 18, wherein the elongated member defines a lumen, and wherein the device further comprises:
an elongated shaft configured to be slidably positioned through the lumen of the elongated member; and
a coupler configured to be positioned at an extracorporeal location when the distal portion of the elongated member is positioned at the treatment site, wherein the coupler is configured releasably fix a position of the elongated shaft relative to the elongated member.

24. The device of claim 23, wherein the elongated shaft has a proximal portion and a distal portion configured to be positioned within the patient's stomach, and wherein the elongated shaft is configured to deliver nutrients to the stomach.

25. The device of claim 18, wherein the treatment site is within a pharynx of the patient.

26. The device of claim 18, wherein the electrical stimulus is configured to treat dysphagia.

27. A device for delivering an electrical stimulus to nerves proximate a body lumen of a human patient, the device comprising:
an elongated member having a proximal portion configured to be coupled to an energy source and a distal portion configured to be positioned at a treatment site within the body lumen, the elongated member defining a lumen therethrough;
a conductive element carried by the distal portion of the elongated member and configured to be electrically coupled to the energy source to deliver an electrical stimulus to nerves proximate the body lumen at the treatment site;
a cover, at least a portion of which is disposed at the distal portion of the elongated member, wherein the cover is movable between (a) a first position in which the cover is positioned over the conductive element, and (b) a second position in which the conductive element is exposed;
an elongated shaft configured to be slidably positioned through the lumen of the elongated member; and
a coupler configured to be positioned at an extracorporeal location when the distal portion of the elongated member is positioned at the treatment site, wherein the coupler is configured releasably fix a position of the elongated shaft relative to the elongated member.

28. The device of claim 27, wherein the cover comprises an elongated shaft configured to be slidably positioned over the elongated member.

29. The device of claim 27, further comprising a retaining structure fixed to the cover and configured to releasably engage the elongated member to fix a position of the cover relative to the elongated member.

30. The device of claim 27, further comprising an interface coupled to the cover and configured to be positioned at an extracorporeal location when the distal portion of the elongated member is positioned at the treatment site, wherein the interface is configured to be manipulated by an operator to move the cover between the first and second positions.

31. The device of claim 27, further comprising a stop configured to engage the cover to releasably secure the cover in the first position.

32. The device of claim 27, further comprising a stop configured to engage the cover to releasably secure the cover in the second position.

33. The device of claim 27, wherein the elongated shaft has a proximal portion and a distal portion configured to be positioned within the patient's stomach, and wherein the elongated shaft is configured to deliver nutrients to the stomach.

34. The device of claim 27, wherein the treatment site is within a pharynx of the patient.

35. The device of claim 27, wherein the electrical stimulus is configured to treat dysphagia.

* * * * *